United States Patent
Johnson et al.

(10) Patent No.: US 10,183,162 B2
(45) Date of Patent: Jan. 22, 2019

(54) COILED, CLOSED-LOOP RF CURRENT ATTENUATOR CONFIGURED TO BE PLACED ABOUT AN IMPLANTABLE LEAD CONDUCTOR

(71) Applicant: Greatbatch Ltd., Clarence, NY (US)

(72) Inventors: Robert Shawn Johnson, North Tonawanda, NY (US); Robert A. Stevenson, Canyon Country, CA (US)

(73) Assignee: Greatbatch Ltd., Clarence, NY (US)

( * ) Notice: Subject to any disclaimer, the term of this patent is extended or adjusted under 35 U.S.C. 154(b) by 429 days.

(21) Appl. No.: 14/986,647

(22) Filed: Jan. 1, 2016

(65) Prior Publication Data

US 2016/0193461 A1 Jul. 7, 2016

Related U.S. Application Data

(60) Provisional application No. 62/099,288, filed on Jan. 2, 2015.

(51) Int. Cl.
| | | |
|---|---|---|
| *A61N 1/08* | (2006.01) | |
| *A61N 1/05* | (2006.01) | |
| *H03H 1/00* | (2006.01) | |
| *H03H 7/24* | (2006.01) | |
| *H03H 7/01* | (2006.01) | |

(52) U.S. Cl.
CPC .............. *A61N 1/08* (2013.01); *A61N 1/05* (2013.01); *H03H 1/0007* (2013.01); *H03H 7/24* (2013.01); *A61N 1/086* (2017.08); *H03H 2001/005* (2013.01); *H03H 2007/013* (2013.01)

(58) Field of Classification Search
CPC . A61N 1/08; A61N 1/05; A61N 1/086; H03H 1/0007; H03H 7/24; H03H 2007/013
USPC .................................................. 607/116, 115
See application file for complete search history.

(56) References Cited

U.S. PATENT DOCUMENTS

| | | | |
|---|---|---|---|
| 7,013,180 B2 | 3/2006 | Villaseca et al. | |
| 7,844,319 B2 | 11/2010 | Susil et al. | |
| 8,244,370 B2 | 8/2012 | Halperin et al. | |
| 8,301,243 B2 | 10/2012 | Stevenson et al. | |
| 2003/0144720 A1 | 7/2003 | Villaseca et al. | |
| 2003/0144721 A1* | 7/2003 | Villaseca | A61N 1/056 607/122 |
| 2013/0338747 A1* | 12/2013 | Kondabatni | A61N 1/05 607/116 |
| 2015/0170792 A1* | 6/2015 | Alford | A61N 1/05 174/102 R |

* cited by examiner

*Primary Examiner* — Michael Carey
(74) *Attorney, Agent, or Firm* — Michael F. Scalise; Marc G. Martino

(57) ABSTRACT

A coiled, closed-loop RF current attenuator is configured to be placed about an implantable lead conductor. A coiled conductor extends in a coiled shape defining a longitudinal axis from a first coil end to a second coil end. The first coil end is electrically connected to the second coil end. An insulator is disposed about the coiled conductor. The closed loop attenuator can also include in series a short, a capacitor and/or a resistor. In some embodiments the closed loop attenuator can be resonant at an MRI RF-pulsed frequency. The closed loop attenuator can be integrated as a permanent part of an implantable lead conductor, or alternatively, be a stand-alone device that is placed about a premade implantable lead conductor.

12 Claims, 14 Drawing Sheets

ACTUAL CIRCUIT

EQUIVALENT CIRCUIT

ACTUAL EQUIVALENT CIRCUIT

ACTUAL CIRCUIT

EQUIVALENT CIRCUIT

ACTUAL EQUIVALENT CIRCUIT

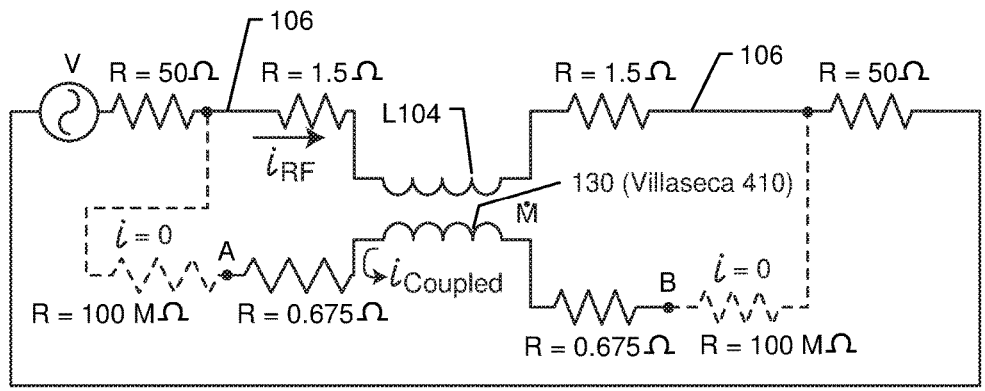
FIG. 13
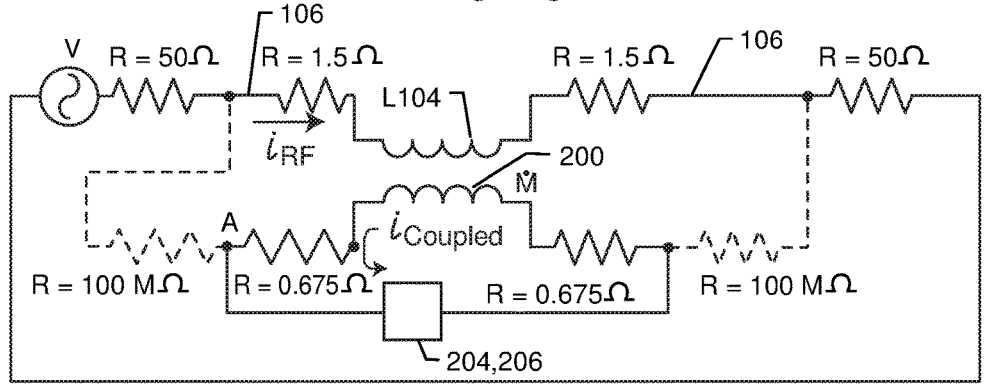
FIG. 14
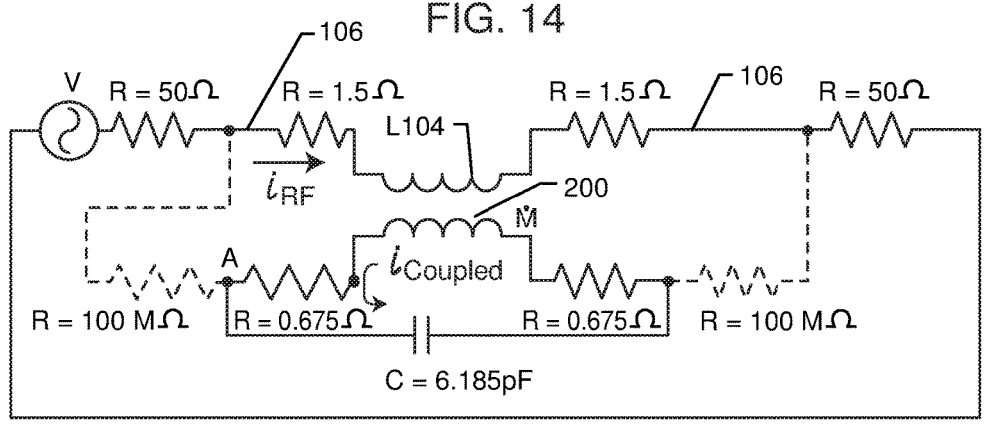
FIG. 15
$$f_r = \frac{1}{2\pi\sqrt{LC}}$$
FIG. 15A

COILED, CLOSED-LOOP RF CURRENT ATTENUATOR CONFIGURED TO BE PLACED ABOUT AN IMPLANTABLE LEAD CONDUCTOR

CROSS-REFERENCE TO RELATED APPLICATIONS

This application claims priority to provisional application 62/099,288 filed on Jan. 2, 2015 the entire contents of which are hereby incorporated by reference.

DESCRIPTION

Field of the Invention

The present invention generally relates to implantable medical leads. More particularly, the present invention relates to a coiled, closed-loop RF current attenuator configured to be placed about a conductor of the implantable medical lead.

BACKGROUND OF THE INVENTION

It is well known in the prior art that implanted leads, inside of a patient, can overheat during exposure to high RF intense fields, particularly those of an MRI scanner. The pulsed RF field of the MRI scanner efficiently couples to certain lengths of implanted leads, thereby inducing substantial currents. These currents can cause overheating at electrodes or at other locations along an implanted lead, thereby presenting a danger to the patient. One is referred to U.S. Pat. No. 8,244,370, the contents of which are fully incorporated herein with this reference. In particular, with reference to the background of the '370 invention, it will be better understood how MRI scanners can induce currents on implantable leads and how said currents can result in a danger to patients. One is also referred to U.S. Pat. No. 8,301,243, the contents of which are incorporated herein by this reference. The '243 patent provides further information as to how MRI scanners can present a danger to patients with implanted lead.

SUMMARY OF THE INVENTION

The present invention is directed to a closed-loop electrical circuit composed of a coiled wire loop, which is formed about an implantable lead conductor. The coiled wire loop is insulated and never makes any direct electrical contact with any conductors of an implanted lead or surrounding tissue.

When an implanted lead is exposed to the intense RF-pulsed fields of an MRI scanner, high currents can result. It is well understood by Faraday's Law of induction and the Biot-Savart law that charges moving at an RF frequency create associated oscillating magnetic fields. For example a 1.5 Tesla MRI scanner uses an RF-pulsed field, whose frequency is based on the Hydrogen Lamour Frequency and would be located approximately at 64 MHz. This means that the current (i) that is induced in one of the conductors in an implanted lead, reverses direction 64 million times per second. This means that the associated magnetic field also reverses it polarity at the same frequency, in other words this magnetic field is expanding and collapsing about the lead conductor at that same frequency.

The wound inductor coil of the present invention intercepts, without making electrical contact, the expanding and collapsing magnetic field, which will induce energy/current (i) in the coil itself. Since energy is conserved the energy in the invention's coil is due to removal of energy from the implanted lead conductor about which the coil is wound. This is typically referred to as magnetic coupling.

In order for the coil to take as much energy out of the implanted lead conductors as possible, it is critical that the coil be a closed loop design. That is, multiple turns of wire, which can be in a single layer or multiple layers are wrapped about an implantable lead conductor or conductors and then the ends of the coil are connected through an impedance such that a complete current (i) loop is formed. It will be taught that the two ends of the closed loop coil can be (1) connected to each other, (2) connected to each other through a resistance or a discrete resistor, (3) connected to each other through a capacitance or a discrete capacitor, (4) connected to each other through a resistance in series with a capacitance or with a discrete resistor in series with a discrete capacitor, (5) connected to each other through an inductance or a discrete inductor and/or (6) connected to each other in combinations of these previous embodiments.

In one embodiment, the ends of the coil will be coupled together through a capacitance such that, the capacitance and the inductance of the closed loop coil are self-resonant at the MRI RF-pulsed frequency. This is not the same as a band-stop filter, as previously taught in U.S. Pat. No. 8,244,370 or in U.S. Pat. No. 8,301,243. In the '370 and '243 patents, indeed, there is an inductor in parallel with a capacitor, which is disposed in series with the conductor of the implanted lead. The present invention is not wired in series with any of the conductors of the implanted lead nor is there any electrical contact made between the conductors of the two constructs. In contrast, the effect of RF energy removal from the lead conductor is through magnetic mutual inductance effects otherwise known as transformer effects or coupling, wherein energy is removed from the lead conductors through mutual inductance coupling (M).

Reference is also made to U.S. Applications 2003/0144720 and 2003/0144721, the contents of which are incorporated herein by this reference. These will hereafter be referred to as the "Villaseca patent publications."

BRIEF DESCRIPTION OF THE DRAWINGS

The accompanying drawings illustrate the invention. In such drawings:

FIG. 13 is a PSPICE representation of the prior art;

FIG. 14 is a PSPICE representation of the present invention with a short;

FIG. 15 is a PSPICE representation of the present invention with a capacitor;

FIG. 15A is the equation of the resonant frequency;

DETAILED DESCRIPTION OF THE PREFERRED EMBODIMENTS

Reference is made to section 3 of ISO Standard 27186 as providing definitions to terms and terminology which are used to describe the present invention. Accordingly, as used herein: "bipolar" means having two poles or electrodes; "connector system" refers to an assembly consisting of a lead connector and a connector cavity that are electrically and mechanically joined; "connector cavity" is defined as a cavity within the pulse generator which is intended to receive a lead connector and an identical cavity within a secondary header; "fixation zone" is a zone located in the lead connector pin and within the connector cavity where the lead connector is mechanically secured within the connector cavity; "high-voltage" is defined as electrical potentials greater than 20 volts up to 2000 volts (Note: High-voltages are generally used for defibrillating the heart); "lead connector" or "plug" is the part of the lead that is intended for insertion into the connector cavity of a pulse generator; "lead connector contacts" are defined as conductive elements on the lead connector which include the lead connector pin and lead connector rings; "lead connector pin" is defined as the most proximal conductive element of a lead connector provided for making electrical contact as well as for securing the lead connector within the connector cavity; "lead connector ring" defines angular conductive elements on the lead connector intended for making electrical contact within the connector cavity (Note: the 4-pole or quadpolar connector (DF4 or IS4) has up to 3 lead connector rings and a lead connector pin); "lead electrode" is the distal part of a lead through which electrical impulses are transmitted to or from cardiac tissue (Note: high-voltage electrodes are capable of delivering high-voltage electrical impulses; Low-voltage electrodes are used for transmitting and sensing low-voltage impulses and are generally not suitable for delivering high-voltage); "low-voltage" defines electrical potentials less than or equal to 20 volts; "pulse generator" is any type of active implantable medical device (AIMD) and particularly those devices that deliver electrical energy to effect cardiac rhythms; "securing mechanism" is defined as a mechanism within the connector cavity intended for mechanically securing the lead connector (Note: a securing mechanism can be an active mechanism, such as a set screw or it can be a passive mechanism, such as a spring contact or self-engaging latch; It can also serve a second function of providing electrical contact with the lead connector, as is the case with a set screw); "tripolar" means having three poles or electrodes.

Figure 1:
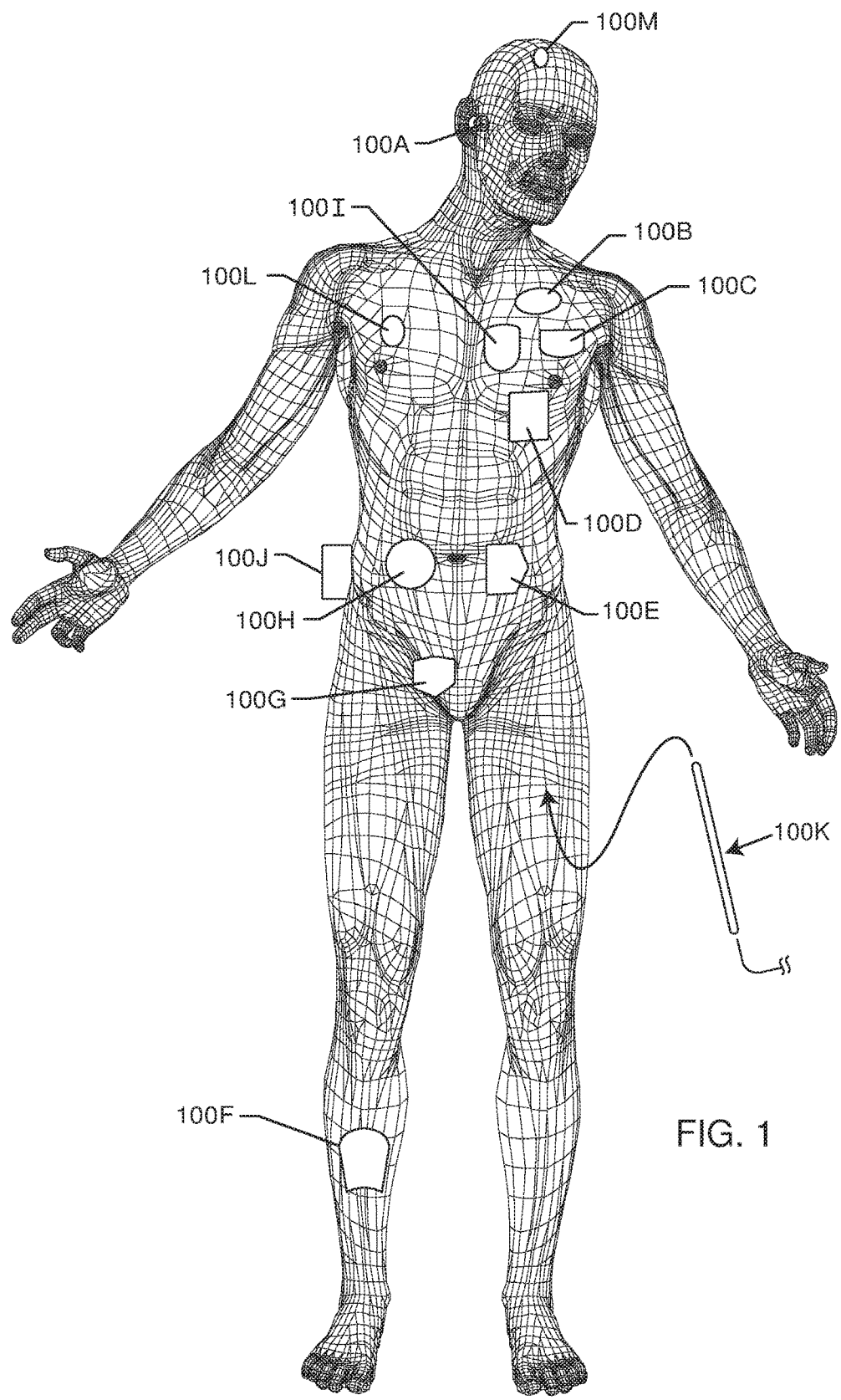
FIG. 1 illustrates a wire form drawing of a human body showing various active implantable medical devices (AIMDs)

FIG. 1 illustrates various types of active implantable and external medical devices 100 that are currently in use. FIG. 1 is a wire formed diagram of a generic human body showing a number of implanted medical devices. 100A represents a family of hearing devices which can include the group of cochlear implants, piezoelectric sound bridge transducers and the like. 100B represents a variety of neurostimulators and brain stimulators. Neurostimulators are used to stimulate the Vagus nerve, for example, to treat epilepsy, obesity and depression.

Brain stimulators are pacemaker-like devices and include electrodes implanted deep into the brain for sensing the onset of the seizure and also providing electrical stimulation to brain tissue to prevent the seizure from actually occurring. The lead wires associated with a deep brain stimulator are often placed using real time MRI imaging. Most commonly such lead wires are placed during real time MRI. 100C shows a cardiac pacemaker which is well-known in the art.

100D includes the family of left ventricular assist devices (LVAD's), and artificial hearts, including the recently introduced artificial heart known as the Abiocor. 100E includes an entire family of drug pumps which can be used for dispensing of insulin, chemotherapy drugs, pain medications and the like. Insulin pumps are evolving from passive devices to ones that have sensors and closed loop systems. That is, real time monitoring of blood sugar levels will occur. These devices tend to be more sensitive to EMI than passive pumps that have no sense circuitry or externally implanted lead wires. 100F includes a variety of bone growth stimulators for rapid healing of fractures. 100G includes urinary incontinence devices. 100H includes the family of pain relief spinal cord stimulators and anti-tremor stimulators. 100H also includes an entire family of other types of neurostimulators used to block pain. 100I includes a family of implantable cardioverter defibrillators (ICD) devices and also includes the family of congestive heart failure devices (CHF). This is also known in the art as cardio resynchronization therapy devices, otherwise known as CRT devices. 100J illustrates an externally worn pack. This pack could be an external insulin pump, an external drug pump, an external neurostimulator or even a ventricular assist device. 100K illustrates the insertion of an external probe or catheter. These probes can be inserted into the femoral artery, for example, or in any other number of locations in the human body. 100L illustrates one of various types of EKG/ECG external skin electrodes which can be placed at various locations. 100M are external EEG electrodes placed on the head.

Figures 2, 3:
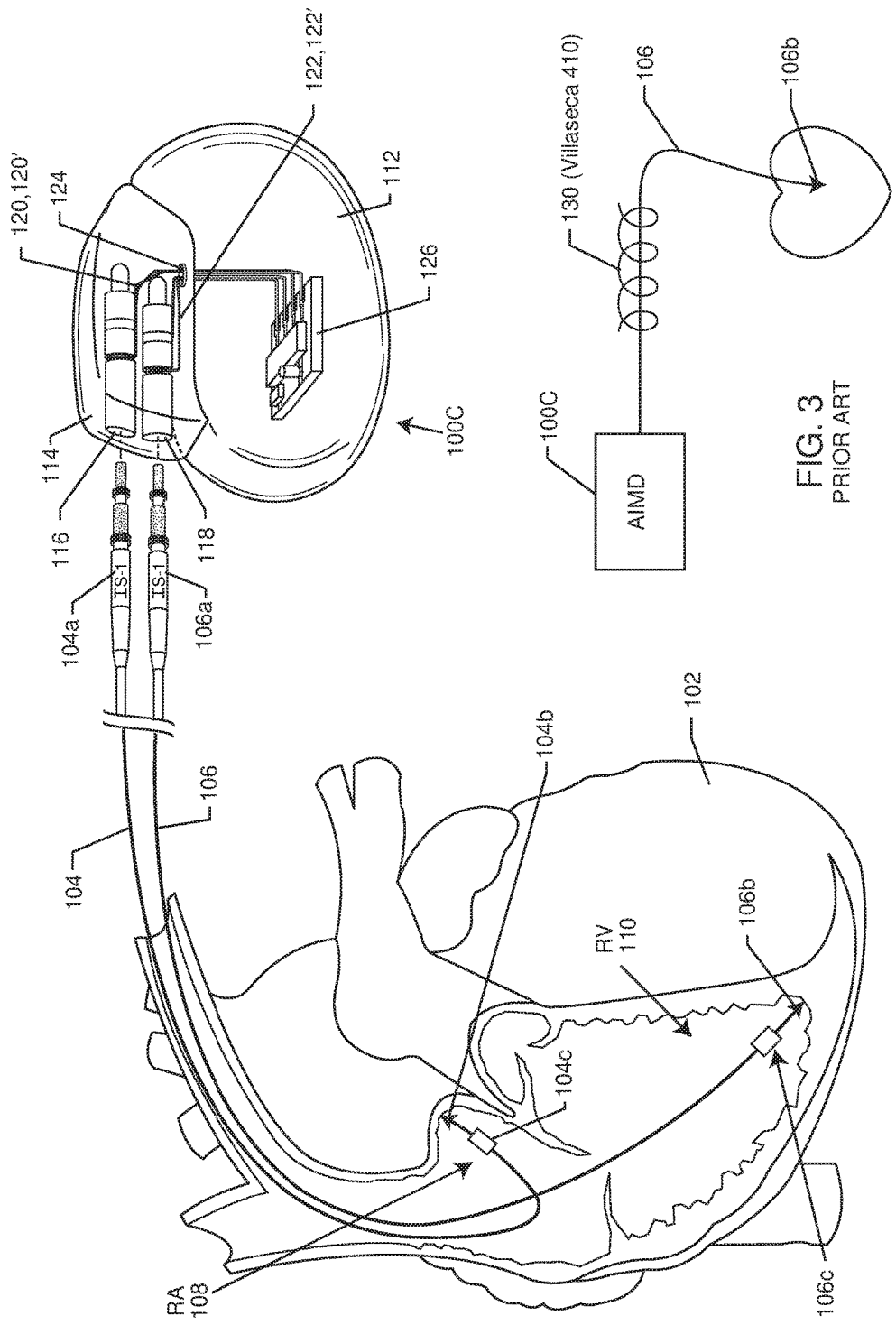
FIG. 2 illustrates a prior art dual chamber bipolar pacemaker with leads implanted into a human heart.
FIG. 3 is a simplified electrical representation of the prior art.

FIG. 2 shows a prior art outline diagram of the human heart 102 and a cardiac pacemaker 100C. Shown are two implanted leads 104 and 106 which both have IS-1 connectors 104a, 106a at their proximal ends. Lead 104 is routed transvenously into the right atrium (RA) 108 of the heart 102. Lead 104 is a bipolar lead, meaning that it has two conductors. One of the lead conductors terminates in the distal tip electrode 104b and the other conductor terminates in the distal ring electrode 104c. Implanted lead 106 is routed into the right ventricular cavity (RV) 110. It is also bipolar, meaning that it has two conductors, one of which is connected to the distal tip electrode 106b and the other conductor is connected to the distal ring electrode 106c. This is known in the art as a dual chamber bipolar pacemaker 100C. The pacemaker 100C has a metallic housing 112 generally of titanium, stainless steel or the like. It also has a header block 114 which holds connector assembly components in accordance with ISO Standard IS-1. In this case, the header 114 has two connector cavities 116 and 118 into which the IS-1 lead proximal connectors 104a, 106a can be inserted. Generally, there would be set screws to fix the connector ring and pin electrodes firmly in place (not shown). There are leadwires 120, 120', 122, 122' routed from the connector cavities 116, 118. These four leadwires 120, 120', 122, 122' are routed to a hermetic seal 124 where the wires pass through the housing 112 in non-conductive relation. It is very important that the housing 112 of the AIMD be completely hermetic to protect sensitive electronic components, for example, those that are shown on circuit board 126.

FIG. 3 illustrates a prior art unipolar lead wire 106 with a distal tip electrode 106b that contacts myocardial cells in a human heart. The proximal end of the lead 106 is connected to an active implantable medical device (AIMD) 100C, which in this case, is an exemplary cardiac pacemaker, as previously illustrated in FIGS. 1 and 2. In a unipolar system, lead 106 only has a single lead conductor or wire. Generally, this lead or conductor is encapsulated in a lead body, which is insulative and also provides mechanical strength properties. Sometimes, these lead conductors (not shown), are helically wound or in other cases can be straight. Some composite lead bodies have both helically wound and straight conductors.

Figure 4A:
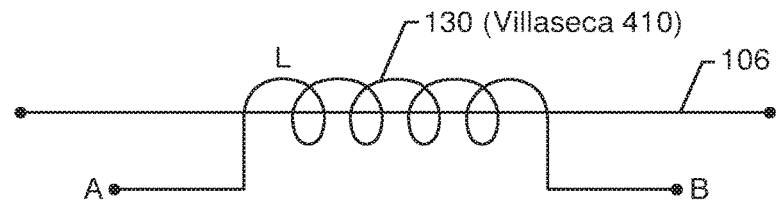
FIG. 4A is a simplified electrical schematic of the actual (physical) circuit of the prior art shown in FIG. 3.
Figure 4B:
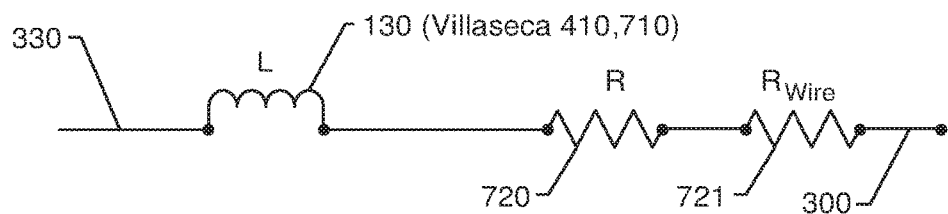
FIG. 4B is a simplified electrical schematic of an incorrectly drawn equivalent circuit of the structure of FIG. 4A.
Figure 4C:
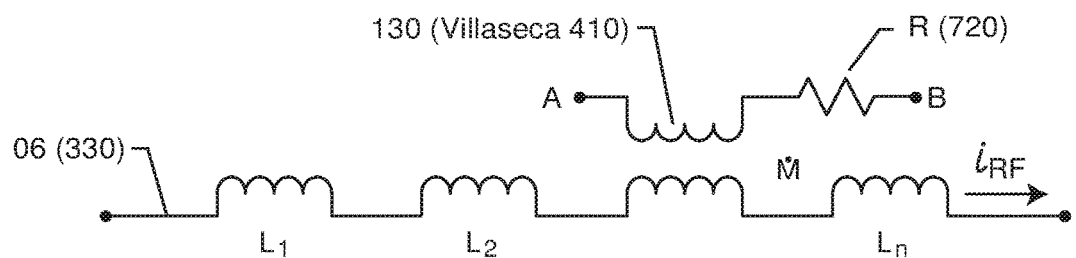
FIG. 4C is a simplified electrical schematic of a correctly drawn actual equivalent circuit of the structure of FIG. 4A.

Referring to the detailed descriptions in the Villaseca references, shown disposed about the lead conductor 106 is a coil 130, which is wrapped about the lead body 106. In either of the Villaseca references their FIG. 4 illustrate a coiled wire 410 disposed about the body of an implanted lead. The following is quoted from paragraph [0030] of the Villaseca '720 reference: "Turning now to FIG. 4, a coil 410 is attached to the lead 300 near the tip 330 of the lead 300. Placing the coil 410 at the distal end 310 of the lead 300 may prevent appreciable amounts of high frequency induced current 340 from traveling on the length 300. Effectively, the coil 410 acts as an electromagnetic trap, which is capable of trapping/filtering RF signal-induced currents 340, such as currents induced by the presence of an MRI signal."

Now, with further reference to the Villaseca '720 publication, the following is quoted from paragraph [0031]: "Turning now to FIG. 5, an enlarged view of the distal end 310 of the lead 300 and the coil 310, is illustrated. The coil is wrapped around lead 300 near the tip 330. The coil 410 provides the function of an inductor, whose inductive properties occur at higher signal frequencies, such as 64/128 MHz." Referring now to paragraph [0032] of the Villaseca '720 publication, it is stated: "Furthermore, an insulative coating 620 that insulates the wire 610 is of dielectric material, such as an enamel coating. Due to the insulation of the coil 410, the portion of the lead 300 covered by the coil 410 is not electrically conducted to its surrounding; therefore, it does not function as an anode or an electrical return path of current into the body of a patient. However, the conductive material 610 of the coil 410 provides for electrical characteristics within the electrical path of lead 300. In other words, the conductive material 610 of the coil 410 adds capacitance and/or inductive characteristics to the electrical path of the lead 300 in a series fashion." (Emphasis added.)

Referring once again to the Villaseca '720 publication, FIGS. 4 and 5 are highly instructive. As clearly stated in quotes from the Villaseca references the open wound coil 410 is electrically insulated from any of the lead conductors. In other words, this is a wrapped coil whose ends are not connected to anything. As a term of art, this is known as an open coil or an open electrical circuit. Indeed, a certain amount of energy will be coupled through the previously described expanding and contracting oscillating magnetic fields due to induced MRI RF currents along lead conductors.

Reference is now made to the Villaseca '720 paragraph [0033], quoting: "Turning now to FIGS. 7a-7b, equivalent electrical circuitry that result from the implementation of the coil 410 onto the lead 300, are illustrated." There are several important things to realize about the above quoted sentence. Most importantly, equivalent circuits, as used in electrical engineering, do not imply a physical circuit. The Villaseca '720 publication clearly states, as quoted above in paragraph [0032], that: "Due to the insulation of the coil 410, the portion of the lead 300 covered by the coil 410 is not electrically conducted to its surrounding, therefore, it does not function as an anode or an electrical return path of current into the body of the patient." (Emphasis added.) In paragraph [0031] of the Villaseca '720 reference, it was stated: "The amount of windings of the coil 410 could be varied to effect the capacitive and inductive effects created by the coil 410." (Emphasis added.)

In this context, as an equivalent circuit model, the words "effect" or "effects" are also very important. In other words, it should not be construed that the open wound coil 410 of the Villaseca '720 reference is in any way physically in series with a lead conductor. Therefore, FIGS. 7a through 7d are significantly in error. For example, in FIG. 7a, an inductor L 710 is shown in series with the implantable lead 300. Furthermore, a resistance 720 is shown, which is very confusing because in the Villaseca '720 paragraph [0033], it is stated: "The coil 410 provides an inductor 720 in series with an equivalent resistance R 710 in the electrical path of the lead 300, which terminates at the ring tip 330." There are obvious typographical errors here in that, the coil is labeled as element L 710 and the resistor is labeled as an element 720. This is further complicated when one reviews the Villaseca '721 reference. In FIG. 7a and paragraph [0036] of this document it is stated: "The coil 410 provides an inductor L 710 with an equivalent resistance R 720 (which in one embodiment is the equivalent resistance of the coil 410) in the electrical lead path of the lead 300." This section seems to imply that the invention's coil 410 has somehow been directly, mechanically, and electrically inserted into the lead, in direct contrast with previous descriptions. These descriptions will confound even one skilled in the art of electrical engineering. It is important and fundamental to recognize that there is no known way in modern, accepted electromagnetic theory or practice to impart a series resistance in the electrical lead 300 using an external influence. In electrical engineering and physics the effects of electrical coupling is termed parasitic capacitance (a term, in fact, used by both Villaseca references) and the effects of magnetic coupling is termed parasitic inductance. Both of these effects are explained in electrical engineering as imparting imaginary impedance. There is no known art which can, without direct electrical contact, place a parasitic real impedance or a resistor in a coupled circuit. The Villaseca references, in contrast to FIG. 7a and 7b, indicate that there is no direct electrical contact between the coil 130 and the lead 106.

The equivalent circuit in Villaseca's FIG. 7b becomes even further confusing in that, it shows an inductor 710 in parallel with a capacitor 730. At first glance, this would appear to be a prior art bandstop filter. One is referred to U.S. Pat. No. 7,844,319 Susil et al., which claims benefit to a provisional application No. 60/283,725 filed on Apr. 13, 2001. FIG. 1g of the Susil reference teaches the use of bandstop filters 24 and 25 in series with a medical lead (in this case, for a probe or catheter used or inserted into human tissues). In Susil, the inductor and capacitor of bandstop filter 24 is truly designed in series with the implantable lead. It is well known by electrical engineers that at resonance an inductor in parallel with a capacitor will present a very high impedance along the length of the lead when it connected to it in series. This has the effect of preventing MRI induced currents from reaching an implanted electrode, for example, the ring electrodes 14 and 15 shown in FIG. 1g of the Susil patent. This is not the case as taught by Villaseca '720.

Referring once again to Villaseca FIG. 7b, this equivalent circuit is simply incorrect. In other words, there is no bandstop filter being physically disposed in series along the length of this lead. In fact, Villaseca '720 makes it very clear that the capacitance C 730 is a parasitic capacitance of the external coil 410 not of the lead 300. One is referred to Villaseca [0036], in which it is stated: "The capacitance C 730 is generally due to the parasitic capacitance that is formed across each of the windings of the coil 410."

Furthermore, in Villaseca '720 paragraph [0037] states: "The capacitance C 730 represents an equivalent capacitance of a combination of the plurality of parasitic capacitance across the linings of the coil 410. The combination of the parallel configuration of the inductor L 710 and the capacitor C 730 provides a parallel circuit that is of a higher impedance than the inductor L 710 by itself. Therefore, the circuit provided by the coil 410 provides for a broader range of frequencies in which significant high impedance at high frequencies is created near the tip 330 of the lead 300."

Again, this is where Villaseca's equivalent circuits are inconsistent. Villaseca '720 never describes, shows or teaches that the coil 410, as illustrated in FIG. 4, is anything, but an open coil. As illustrated in Villaseca's FIG. 5, the two ends of the coil 410 are not connected together. Villaseca further teaches away from the idea that the ends of the coil are connected together when he describes that the capacitance C 730 of FIG. 7b, is a parasitic capacitance formed among adjacent windings of the coil. In other words, the equivalent circuit, as illustrated in FIG. 7b, wherein a bandstop filter is disposed in series along the lead conductor 300, is not a physical reality. As previously pointed out, the Susil '319 patent clearly illustrates in its FIG. 1g, the physical reality of a bandstop filter disposed in series of medical lead conductors 4 and 5. A major limitation of the Villaseca '720 publication is that the ends of the physical coil 410 are open and return currents are limited to the parasitic capacitance C formed by the inductor L. For an open wound coil such as shown in the Villaseca '720 FIGS. 4 and 5 the parasitic capacitance that appears between each of the insulated winding, will not result in a high enough loop current (i) to transfer substantial amounts of induced RF energy out of the implanted lead 300 and into the coupled structure, as described by Villaseca. By leaving open the end of the coil a large impedance exists between points A and B of FIG. 4A. When the RF currents in the lead 106 magnetically couple to the coil 130 a voltage will be induced across the length of the coil as described by Faraday's Law of Induction. Since the ends (A and B) of the coil 130 are not connected, no further current will be able to flow. The power associated with the induced effects in the coil 130 can be expressed as P=I×V where, P is power dissipated in the coil 130, I is the current induced in the coil 130, and V is the voltage induced across the coil 130. Since the current is zero no appreciable power can be present in the Villaseca invention of coil 130. PSPICE simulations will be provided herein to further prove this effect.

FIGS. 7c and 7d are equivalent circuits in Villaseca '720, which are also highly misleading and inconsistent with accepted electrical engineering principals. The open wrapped coil, indeed at low frequency, would appear invisible to electrical currents. Therefore, the only equivalent circuit that the inventors herein agree with would be FIG. 7c wherein, at low frequency, the only effect along the length of the medical lead conductor 300, is its own resistance 720. In other words, this is the resistance of the lead conductor and is not affected in any way by the loosely, open wrapped coil. At low frequency, the inductive effect of the loosely, open wrapped coil, including any mutual inductance, would be trivial. However, in FIG. 7d, it is implied the equivalent circuit at high frequency is an open circuit and this is simply not true. One of the reasons for this is that the bandstop filter, as described in FIG. 7b of Villaseca '720, is not in series with the lead conductor 300. Again, one has to go back to the Susil reference to see that teaching as well as U.S. Pat. No. 8,244,370, which has priority to provisional application No. 60/283,725 filed on Apr. 13, 2001. In other words, it has been long known that placing bandstop filters in series with medical leads would provide a very high impedance (ideally, an infinite or open circuit) at an MRI RF-pulsed frequency. The equivalent circuit of FIG. 7d is literally taken from Susil FIG. 1e where the electrodes 14 and 15 are cut or cut off from the lead conductor such that no RF currents can flow into human tissue. This is simply not possible with the open wound coil 410 of Villaseca, particularly when the return circuit is solely dependent on miniscule amounts of turn-to-turn capacitance. In the present invention, it will be taught that it is very important to wrap a coil about medical leads and have the two ends of that coil terminated in an impedance. It will also be demonstrated that the selection of that impedance is very important in order to maximize currents to the coil and thereby, transfer a maximal amount of RF energy out of the lead body and trap it in the closed loop coil of the present invention.

FIG. 4A of the present invention is the electrical engineering accepted Villaseca circuit (Villaseca FIGS. 4, 5 and 6) showing the coil 130 (Villaseca 410) wrapped around the lead conductor 106. FIG. 4B is shown as an equivalent circuit and as previously noted, resistor R 720 is actually a subset of the resistance of the lead wire $R_{wire}$ 721 and not induced by the open wound coil 130. FIG. 4B is reproduced using the same numbering as in the Villaseca reference. As previously described, the resistance $R_{wire}$ 721 and the resistance R 720 actually refer to the same equivalent series resistance of the implanted lead conductor 330, which is described as the lead conductor 106 in the present invention. Referring once again to FIG. 4B, one can see that the inductor L is labeled as 130 (Villaseca's 410, 710). The 410 refers to the open wound coil as described in Villaseca '720 FIGS. 4 and 5 and 710 refers to the effect that the open wound coil has upon the implanted lead wire 106, which is shown in FIG. 4B as Villaseca 330. The inventors herein, agree that the open wound coil of Villaseca will have a small inductive type of affect (due to mutual inductance) on the implanted lead 330. However, this affect will be miniscule as opposed to the present invention as will be further described herein.

Figure 5A:
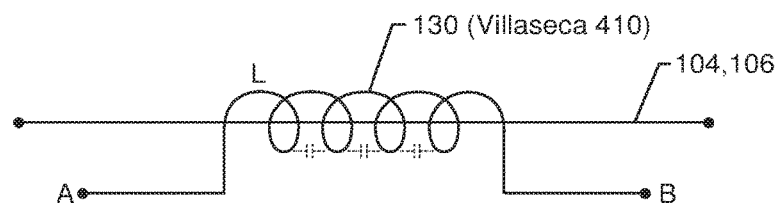
FIG. 5A is similar to FIG. 4A, which is another simplified electrical schematic of the actual (physical) circuit of the prior art shown in FIG. 3.

FIG. 5A is the actual circuit of Villaseca '720 showing the inductor L 130 (410). As one can see, the two opposite ends of the inductor A and B are not connected to each other or to any other component. Nowhere in Villaseca '720 is it taught that there is an impedance element connected between points A and B.

Figure 5B:
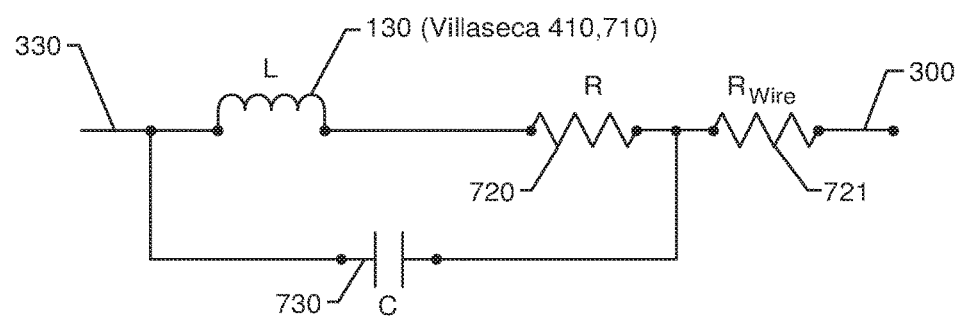
FIG. 5B is a simplified electrical schematic of an incorrectly drawn equivalent circuit of the structure of FIG. 5A.

FIG. 5B is taken from Villaseca's '721 FIG. 7b equivalent circuit and is not the appropriate equivalent circuit of the effect of Villaseca's open wound coil about the lead wire will have on the lead wire 300. As previously described, it is not appropriate to break open the implanted lead wire 330 and insert a discrete inductor in parallel with a discrete capacitance C into the AIMD lead wire(s). In particular, there is no known electrical engineering principle to couple in the resistance 720 into the lead wire 300. Villaseca incorrectly states that this will present a very high impedance in series with the lead 330 (herein known as implanted lead 106). As previously described the open wound coil will not support sufficient currents to allow a large amount of power to be present in the invention's coil 130 and by conservation of energy large amounts of the energy cannot be removed from the lead 300. In addition, such bandstop filters have already been taught by Susil and the other references cited that predate Susil.

Figure 5C:
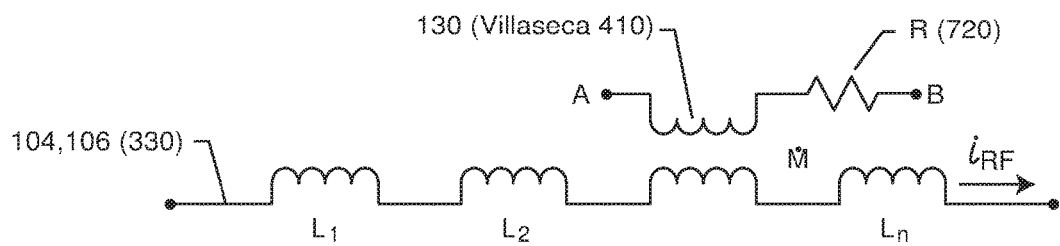
FIG. 5C is a simplified electrical schematic of a correctly drawn actual equivalent circuit of the structure of FIG. 5A.

FIG. 5C illustrates the actual equivalent circuit that should have been drawn by Villaseca. Shown, is an implanted lead 106 (described as element 330 in Villaseca). This lead can either be helical (coiled) or a straight filar. In either case, it is known through the Biot-Savart law that an AIMD implanted lead would have distributed inductances along its entire length shown as $L_1, L_2 \ldots L_n$. Now, in any one of these locations, you could apply at any point along the lead 106 the open wound coil 130 (410 of Villaseca). There is a mutual inductance (M) indicating that the expanding and collapsing magnetic field, due to RF currents in the lead, shown as $i_{RF}$. Those expanding and contracting lines of magnetic field would also cut across the wires of coil 130 (410). The mutual inductance, in this case, is quite small compared to a conventional transformer, because there are no ferromagnetic materials involved. The reason for this is because of the main static field of an MRI scanner. The 1.5 Telsa or greater static magnetic field would saturate and render such ferromagnetic materials useless for this particular application. Referring back to FIG. 5C, it will be appreciated that all along the length of the lead conductor 106, there are not only inductances $L_1, L_2 \ldots L_n$, but there are also distributed resistances all along its length. It's impossible to know, from the description of Villaseca '721 whether this resistance is R 720 or R 721. One thing that is clear, for the open wound coil 410 of Villaseca, it is simply not possible to impart a real impedance (resistance) in series with the resistance of the lead conductor 106. That would be an improper equivalent circuit.

It is particularly interesting to study U.S. Pat. No. 7,013, 180, the contents of which are incorporated herein by reference, which is the patent that issued from the Villaseca publication 2003/0144721. The inventors have gone through a lot of effort to explain how the Villaseca publications and patent do not in any way teach that the open wound coil inductor 410 has any direct connection to a lead wire. Direct quotes from the Villaseca specification make it clear that coil 410 is insulated, does have parasitic capacitance and is not electrically connected to any lead or body tissue. In this light, it is most constructive and most confusing to examine Villaseca's patent claim 1 against Villaseca's patent claim 2. In claim 1, it is clearly stated, "A first coil wound about at least one of said proximal end portion." In this case, the word "about" is key. This is completely consistent with Villaseca's entire spec where his coil 410 is wound about the lead body or lead connector. This is also completely inconsistent with Villaseca's claim 2, which states, "A medical electrical lead comprising: a pacing tip; a connector adapted for connecting with an implantable device connector block; an electrical flow path extending between the connector end and the pacing tip; and a plurality of inductive coils, each in series with the electrical flow path; wherein, at least one of the plurality of inductive coils is adapted to filter RF signal-coupled electrical energy traveling along the flow path towards the pacing tip."

The plurality of inductive coils each in series with the electrical flow path, is exactly what was taught in the Susil reference in FIG. 1f wherein, coils 24 and 25 are shown disposed physically and electrically in series with the electrical flow path. The coil of Villaseca 410 has an inductive "effect" on a lead, but does not literally create a plurality of inductive coils in series with the electrical flow path. This gets even more confusing when one reads Villaseca's claim 5 as it reads on claim 2 wherein, it states, "The lead of claim 2, further comprising a capacitor in parallel with a one of the plurality of inductor coils." Villaseca never teaches or suggests a discrete capacitor. In fact, this is exactly what is taught by Susil FIG. 1g wherein, a bandstop filter is disposed as an inductor in parallel with a capacitor in series with the conductive path. In summary, claims 2 and 5 of Villaseca were already taught by Susil in U.S. Pat. No. 7,844,319 and by Halperin/Stevenson in U.S. Pat. No. 8,244,370 (which has priority back to 2001). In addition, Villaseca's claim 1, which describes a coil about the lead, is completely inconsistent with claims 2 and 5. Villaseca seems to be claiming two completely different inventions, which is confusing to the present inventor.

Figure 6:
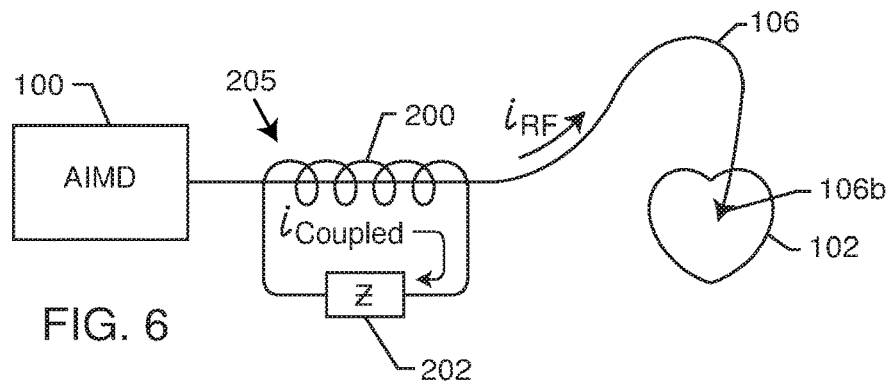
FIG. 6 is a simplified electrical representation of one embodiment of the present invention.

FIG. 6 illustrates the lead system of the present invention. Shown is an AIMD 100. Referring back to FIG. 1, AIMD 100 can be any of a number of AIMDs, as described in FIG. 1. Exemplary lead body 106 is shown. In this case, the lead is unipolar, meaning that it only contains one conductor. It will be appreciated that unipolar is shown for simplicity, but any number of AIMD implantable lead conductors are equally applicable. By way of illustration, an electrode 106 is shown inside of a human heart 102. But it will be appreciated that this could be a neurostimulator, for example, a spinal cord stimulator, a deep brain stimulator or the like. Again, refer to FIG. 1 for examples of all the different AIMD lead systems, including probes and catheters that the present invention is applicable to. A closed loop coil 200 of the present invention is shown wound around the lead conductor 106 wherein, its two ends are terminated in an impedance element Z 202. This is a major distinction from Villaseca in that, the two ends of Villaseca's coil A and B are never shown connected together or to anything else as is specifically stated in the Villaseca specification.

Figure 7:
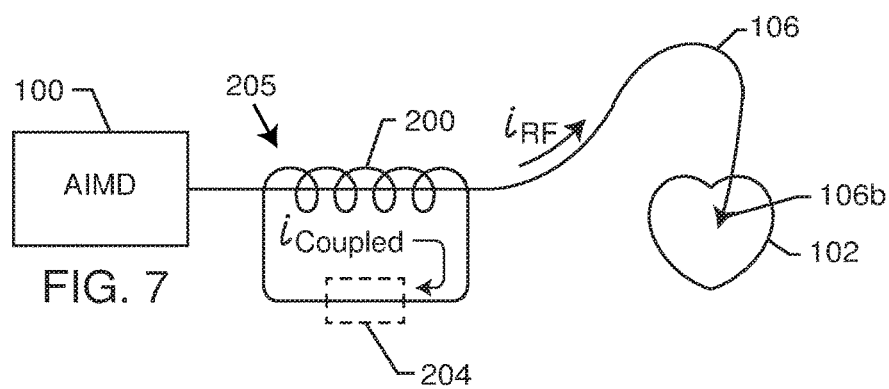
FIG. 7 is a simplified electrical representation of another embodiment of the present invention with a short.

FIG. 7 is identical to FIG. 6 except that the impedance element has been replaced by a short circuit 204. In other words, the two ends of the coil A and B are simply connected together.

Figure 8:
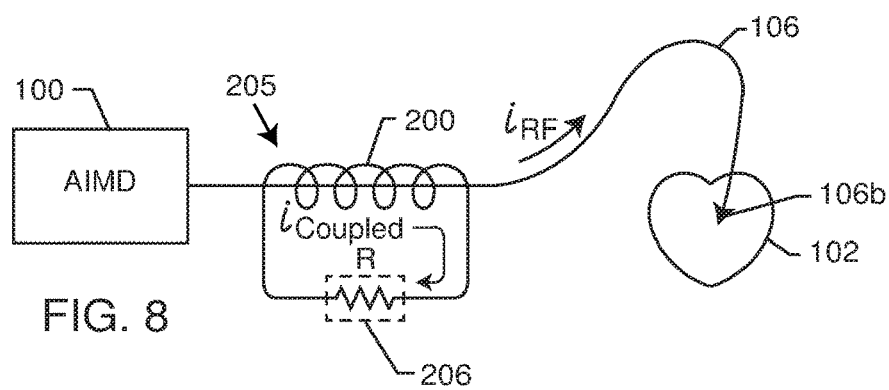
FIG. 8 is a simplified electrical representation of another embodiment of the present invention with a resistor.

FIG. 8 is also very similar to FIGS. 6 and 7 except that in this case, the impedance element Z is a resistor R 206.

Figure 9:
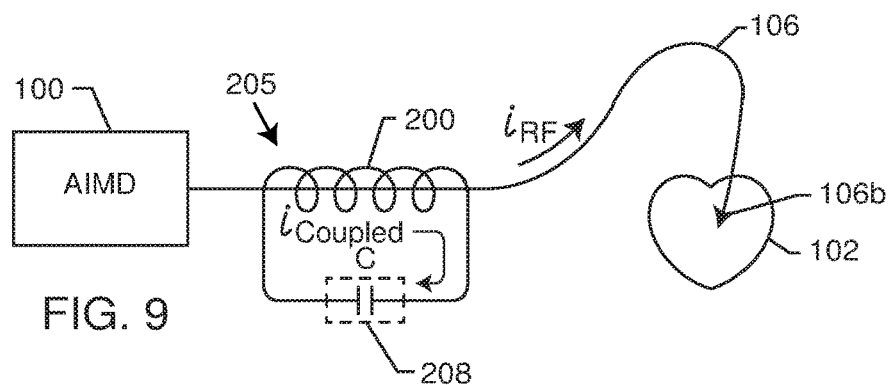
FIG. 9 is a simplified electrical representation of another embodiment of the present invention with a capacitor.

FIG. 9 is very similar to FIGS. 6, 7 and 8 except that in this case, the impedance element is a capacitor C 208.

Figure 10:
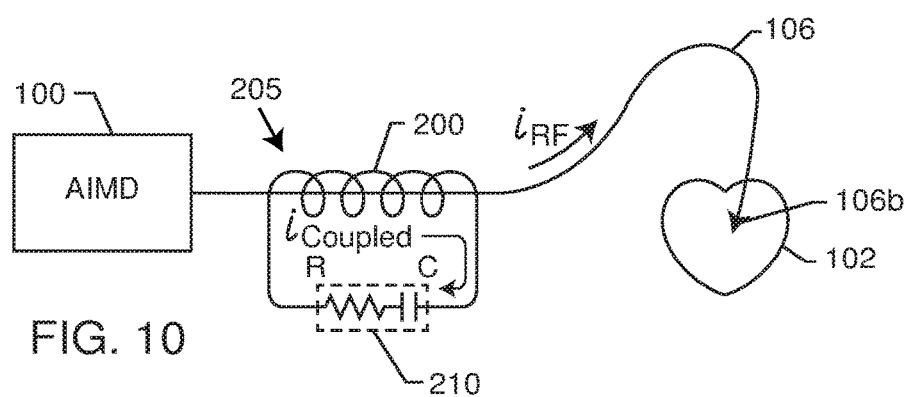
FIG. 10 is a simplified electrical representation of another embodiment of the present invention with a resistor and capacitor.

FIG. 10 is very similar to FIGS. 6, 7, 8 and 9 except that in this case, the impedance element Z is a resistor R in series with a capacitor C 210.

Figure 10A:
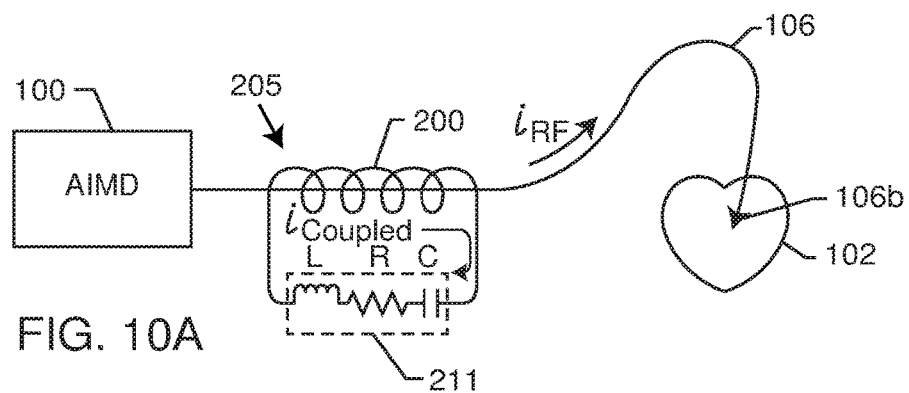
FIG. 10A is a simplified electrical representation of another embodiment of the present invention with an inductor, a resistor and a capacitor.

FIG. 10A illustrates the impedance element 211 where an inductor L placed in series with a resistor R and a capacitance C, indicating that an inductor chip can be added. It will be appreciated that an inductor chip or discrete inductor element or component could be added to any of the closed loop circuits as illustrated in FIGS. 6 through 10. This is particularly useful when the inductance of the wound inductor 200 is not very large and an improved L/C ratio is required to better optimize the impedance of the closed loop coil of the present invention at resonance.

Referring to FIGS. 6 through 10A, in every one of these embodiments, through mutual inductance, a significant amount of induced RF energy along the lead conductor 106 is transferred to the closed loop coil 200 of the present invention. In every embodiment, it is preferred that as much current ($i_{coupled}$) as possible flow in this closed loop circuit comprising the coil 200 and the connecting impedance Z. This robs energy from the lead conductor 106 thereby lowering the energy present at the interface between the distal electrode 106 and body tissues, limiting the possibility of overheating and potential damage. In an embodiment, it will be appreciated that the closed loop inductor attenuating filter of the present invention, be disposed at or near the one or more distal tip electrodes 106b.

The COILED, CLOSED-LOOP RF CURRENT ATTENUATOR CONFIGURED TO BE PLACED ABOUT AN IMPLANTABLE LEAD CONDUCTOR will hereinafter be referred to as the "closed loop attenuator" for the sake of simplicity. It will be appreciated that this shorthand way of describing the invention is fully describing the closed loop system or circuit, including a connecting impedance, as previously described in FIGS. 6 through 10A.

Figure 11A:
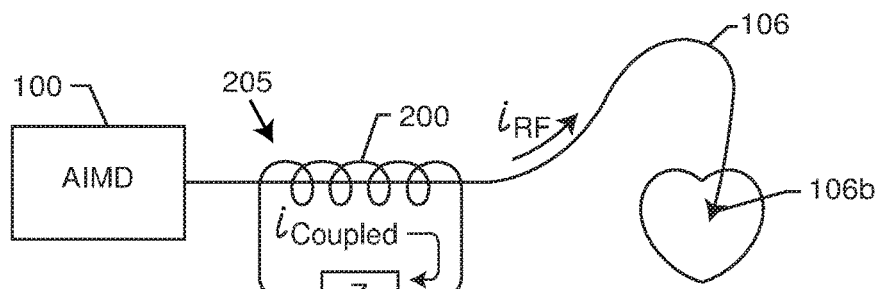
FIG. 11A is a simplified electrical representation of another embodiment of the present invention now placed about a unipolar lead.

FIGS. 11A through 11E illustrate the closed loop attenuator of the present invention and how it can be applied to various lead systems. In FIG. 11A, it is shown that the closed loop attenuator 200, 202 can be placed anywhere along the length of a unipolar lead 106. From this point on the closed loop current attenuator of the present invention, will be referred to as a single number 205. It will be understood that the closed loop current attenuator 205 always encompasses a coil 200 wrapped around at least one AIMD lead conductor, where its two ends are terminated in an impedance element 202, which can embody any of the impedance elements previously described in FIGS. 6 through 10A.

Figure 11B:
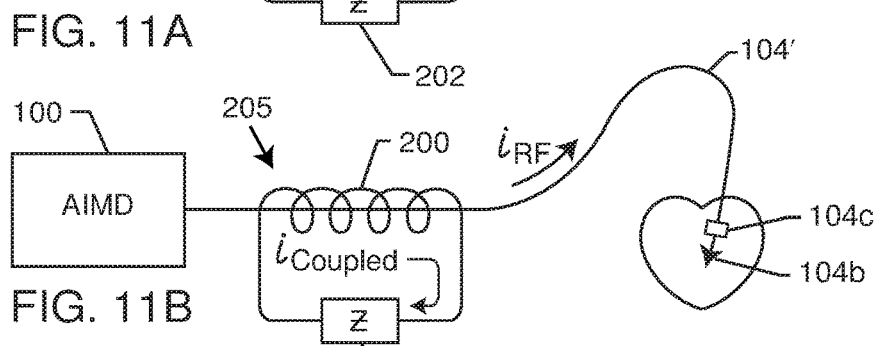
FIG. 11B is a simplified electrical representation of another embodiment of the present invention now placed about a bipolar lead.

In FIG. 11B, it is shown that the closed loop attenuator 205 can be placed anywhere along the length of a biopolar lead system 104'. In a bipolar lead system, there is generally a tip electrode 104b and a ring electrode 104c. This means that the lead body 104' actually has two conductors running from the AIMD, one conductor terminates at the distal tip electrode 104b and the other conductor terminates at the ring electrode 104c. It is very common for pacemaker applications that both of these conductors are spirally (helically) wound, one inside the other. A closed loop attenuator of the present invention therefore, becomes very well coupled to the lead conductors because its closely spaced turns are wound directly around the turns of the bipolar lead. Having spiral or helically wound implantable lead conductors, creates a stronger oscillating magnetic field as opposed to straight wires. Straight wires are commonly used in defibrillator applications or in neurostimulator applications. The present invention is still very effective for those, but it is even more effective when AIMD lead conductors are helically wound.

Figure 11C:
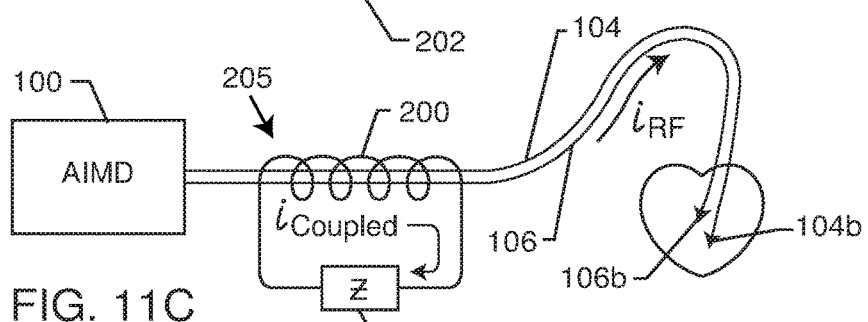
FIG. 11C is a simplified electrical representation of another embodiment of the present invention now placed about two unipolar leads.

FIG. 11C illustrates that the closed loop attenuator 205 of the present invention can be wound over multiple lead bodies. In this case, there are two lead bodies 104 and 106 each of which contains a unipolar conductor, which are connected to electrodes 104b, 106b at their distal ends.

Figure 11D:
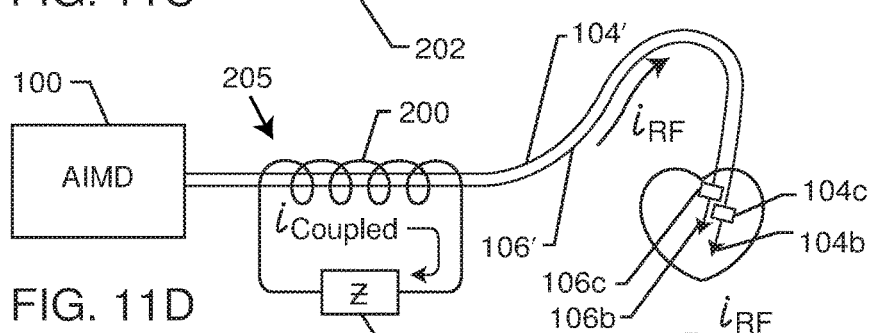
FIG. 11D is a simplified electrical representation of another embodiment of the present invention now placed about two bipolar lead.

FIG. 11D illustrates the same system as FIG. 11C except that each of the lead bodies 104' and 106' are bipolar, meaning that each lead is associated with its own distal tip (104b, 106b) and distal ring electrode (104c, 106c). This is the system that was more thoroughly described as the dual chamber pacemaker, in FIG. 2.

Figure 11E:
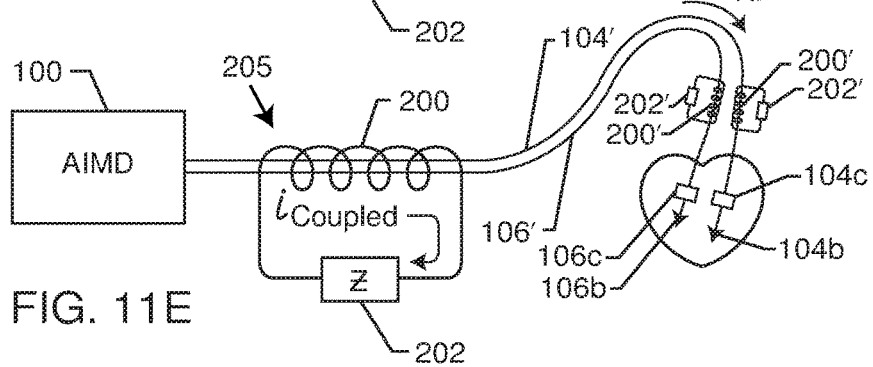
FIG. 11E is a simplified electrical representation of another embodiment of the present invention now placed about each of the two bipolar leads near their distal tips and also placed about both the leads together at their proximal end.

FIG. 11E illustrates that the closed loop attenuator 205 of the present invention can be wrapped around a bundle of leads 104' and 106' or it can be wrapped around the lead body separately.

Figure 12:
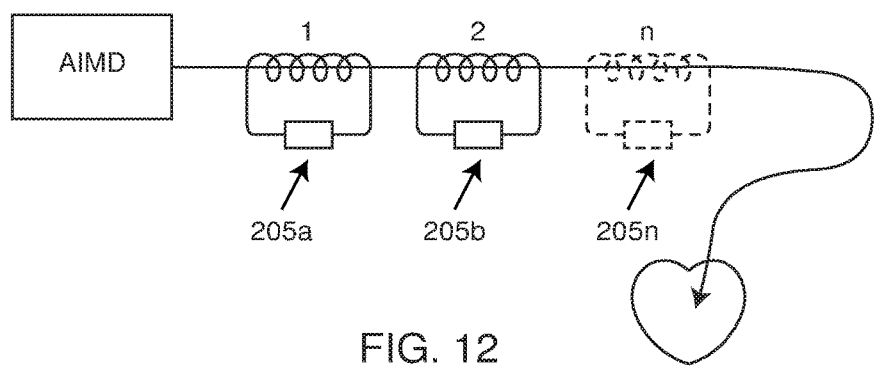
FIG. 12 is a simplified electrical representation of how the present invention can be placed anywhere along the length of a lead.

FIG. 12 illustrates that any number of the current attenuators 205 of the present invention can be placed along a lead conductor or locations, $205a$, $205b$ . . . $205_n$. It is also understood that the unipolar lead illustrated in FIG. 12 could be a bipolar lead, or be a multiplicity of leads having any number of conductors.

FIGS. 13 to 15 shows schematic captures of PSPICE simulation circuits. Three circuits were created and simulations were performed, which will later be plotted and compared to show how effective the closed loop attenuator 205 of the present invention is compared to Villaseca's open loop coil. FIG. 13 is a PSPICE schematic of Villaseca's circuit. The Villaseca coil 130 (described by Villaseca as coil 410) is shown adjacent to distributed inductance L 104 of the implanted lead 106. It will be appreciated through the Biot-Savart law in physics, that all conductors will have a distributed inductance along their length. For adjacent conductors, a mutual inductance M exists. Now referring to the PSPICE schematic, a voltage source is shown driving a standard 50-ohm source and 50-ohm load resistance. A 50-ohm source and load are representative of most common test equipment, such as Spectrum or Network Analyzers. In other words, this simply represents applying a network analyzer to analyze the lead system and the open wound coil of Villaseca.

Referring again to FIG. 13, points A and B of Villaseca are not connected as Villaseca describes. However, one will notice in the PSPICE simulation that a 100-MΩ resistance is shown connected between point A and lead conductor 106 and another 100-MΩ resistance is connected between point B and lead conductor 106. The reason for this is to "fool" PSPICE. The PSPICE schematic and simulation software will not allow open or floating nodes. In other words, the program will not run if there is a dangling node like node A or B left unconnected or floating. The electrical design engineer "fools" the program by placing a very high value of resistance like 100-MΩ between the elements that they wish to electrically isolate. This could have been 100-GΩ or 100-TΩ, but the important thing is that the value be so large that it will not affect the circuit simulation result. In summary, PSPICE does not recognize an infinite resistance and simply will not run if a node is left unconnected. As will it be shown in a subsequent drawing, the plotted currents in the Villaseca coil 130 (410) will be shown in comparison to two of closed loop attenuator designs of the present invention.

FIGS. 14 and 15 are PSPICE schematics of the embodiments illustrated in FIGS. 8 and 10 herein. It will be appreciated that for the ideal embodiments, shown in FIGS. 7 and 9 wherein, there is no resistance, however these are ideal since some resistance is always present due to the materials used to construct the coil. The PSPICE circuit, shown in FIG. 14, has an impedance element 204,206. Element 204 represents a short circuit and 206 represents that even a short circuit will have some resistance, particularly when one includes the 1.35Ω of resistance that would be the resistance of the coil of the closed loop attenuator 200. Again, 100-MΩ resistors are used to "fool" PSPICE and to electrically isolate, except for the mutual inductance between the coil 200 and the inductor L104 of the lead 106, the closed loop attenuator 205 of the present invention from the rest of the circuit which represents the lead 106 with induced RF current ($i_{RF}$). Accordingly, FIG. 14 is applicable to a short circuit, as shown in FIG. 7, or a resistance, as shown in FIG. 8 (204,206).

FIG. 15 is similar to FIG. 14 and it shows the closed loop current attenuator 205 of the present invention, but in this case the circuit includes a discrete capacitance of 6.185 picofarads. This capacitance has been carefully calculated with the inductance of coil 200 to create a resonant circuit at 64 MHz.

For FIGS. 13, 14, and 15 the coil of the respective inventions, 130 (Villaseca 410) and 200, is simulated as a 1.0 microHenry inductor with a PSPICE coupling factor of 0.5 to the L 104 of the lead 106 which is simulated as a 0.1 microHenry inductor.

In FIG. 15, the value of the discrete capacitance has been carefully calculated to include any parasitic capacitance that is also present in coil 200. In this way, the capacitor C 208 is resonant with the inductor 200 and the MRI pulsed frequency of about 64 MHz for a 1.5T Hydrogen imaging MRI. This is not actually thought of as a bandstop filter as erroneously portrayed by Villaseca. In practice this circuit is actually an inductor in series with a capacitor. The objective of FIG. 9 to 10A is minimize the impedance of the circuit when it is at resonance. The configuration of this invention is considered a bandpass circuit as opposed to bandstop whose objective is to maximize the impedance of the circuit when it is at resonance.

To describe resonance the following conventions are used: (1) the inductive reactance is designated as a +j inductor sign and (2) the capacitive reactance is designated as a −j reactance sign. Resonance occurs when $-jX_C=+jX_L$ wherein $X_C$ is the capacitive reactance and $X_L$ is the inductive reactance. FIG. 15A gives the formula for the resonance frequency $f_r$ in Hertz wherein, the inductance is in henries and the capacitance is in farads. The values of L and C are carefully chosen, such that the resonant frequency $f_r$ will occur at the MRI RF-pulsed frequency. In other words, for a 1.5 Tesla scanner, $f_r$ would be 64 MHz. At resonance the impedance of the inductor and capacitor cancel and appear as a short circuit, allowing maximum current to flow in the loop. Another way of looking at this is maximal energy will be robbed from the implanted lead conductor when the closed loop attenuator 205 is at resonance.

Figure 16:
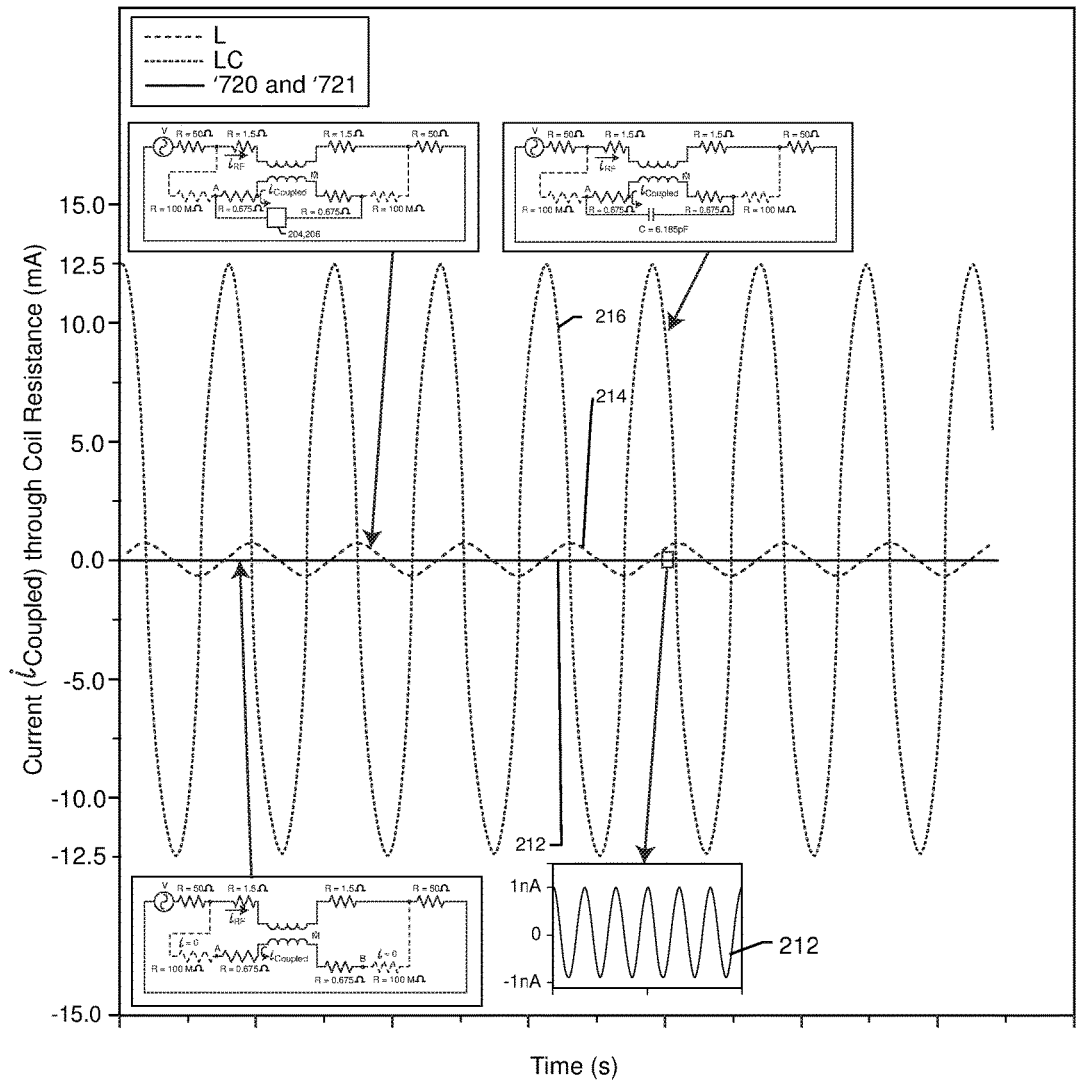
FIG. 16 is a plot of the electrical schematics of FIGS. 13-15.

FIG. 16 illustrates a family of curves, which are PSPICE simulations of the schematics previously illustrated in FIGS. 13, 14 and 15. From FIG. 16 the curve with the least amplitude appears as a flat line, expect in the zoom-in window, illustrates the amount of current 212 ($i_{coupled}$) that will flow through Villaseca's open circuit coil 130 (410). The current that is induced in Villaseca's open loop coil 130 (410) is illustrated in FIG. 16 as 212. Element 212 is also shown in a blown-up box showing that the current ($i_{coupled}$) induced in Villaseca's coil is very small due to the coil 130 being an open circuit where end A and B of FIG. 4 are not connected and is on the order of nanoamperes. This small current is what is required to create the voltage drop across the coil 130 due to coupling with the lead inductance 104. This is a trivial amount of current (icoupe), meaning that a trivial amount of energy has been robbed, due to mutual inductance, from the implantable lead system.

In comparison, curve 214 illustrates the closed loop attenuator of the present invention, with the return impedance as a short circuit or as a resistance. In this case, a resistance of 1.35 ohms is shown, generally representing the resistance of the coil 200 itself. As one can see, this induces a significantly larger coupled current 214 ($i_{coupled}$), as compared to Villaseca 212, but is still small compared to the amount of current ($i_{coupled}$) that can be achieved through a resonant circuit using a discrete capacitor connected between the ends of the coil A and B. Attention is drawn to curve 216 which represents the current ($i_{coupled}$) induced in the coil 200 that is resonant with capacitor 208. One can see that the current ($i_{coupled}$) is many orders of magnitude greater (approximately 12.5 milliamps) as compared to the nanoamps of the Villaseca open circuit design.

In summary, the closed loop attenuator 205 of the present invention, when designed to be resonant with an external capacitance, creates a maximal current in coil 200 thereby transferring maximal energy out of the lead thereby, making the lead safer. In particular, when disposed at or near a distal tip electrode this has the effect of lowering the RF energy present at a distal tip electrode thereby greatly reducing the chance that it could overheat, burn or otherwise injure sensitive body tissue, such as nerves.

Figure 17:
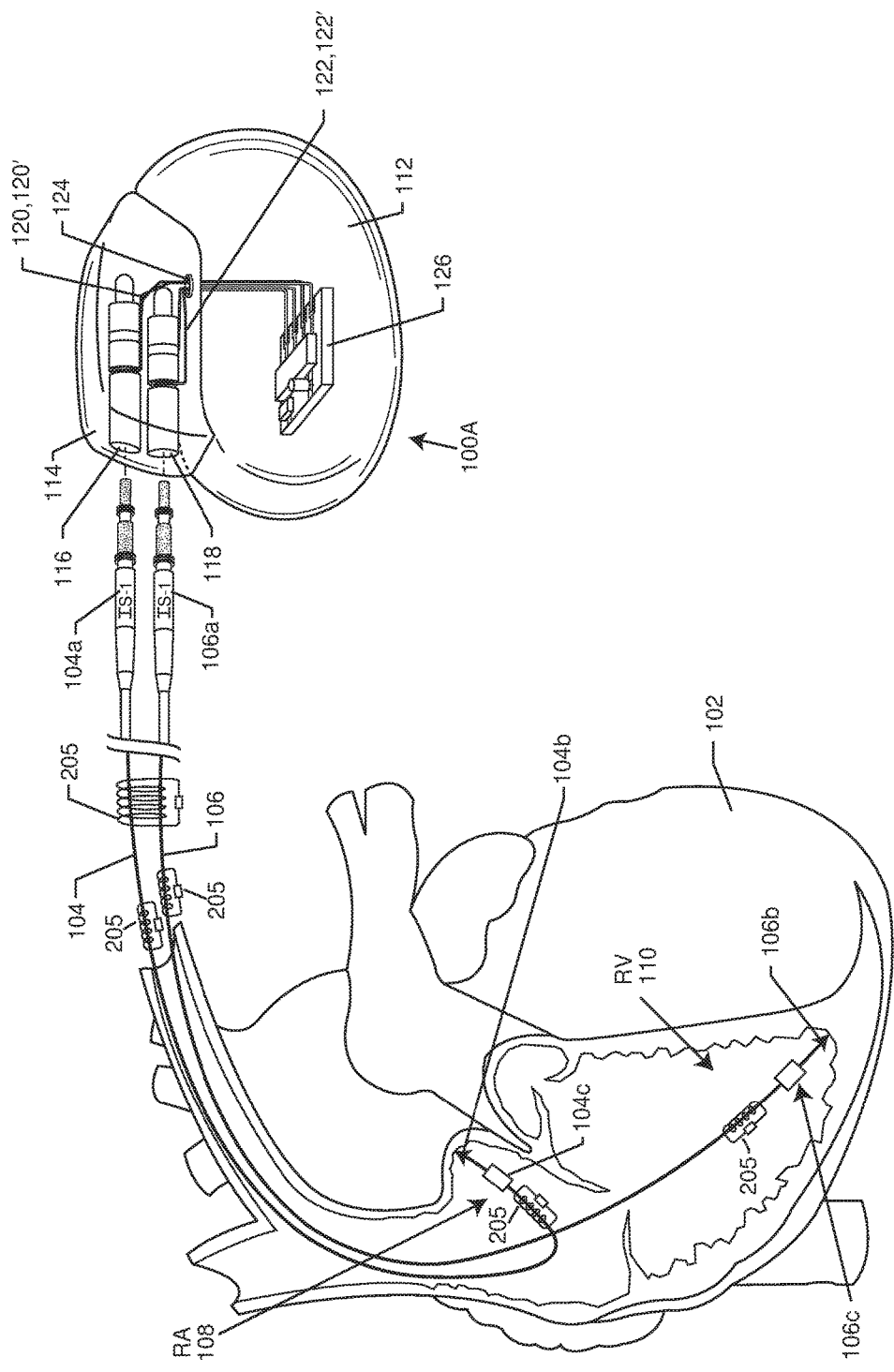
FIG. 17 is similar to FIG. 2 and illustrates a prior art dual chamber bipolar pacemaker with leads implanted into a human heart now showing the present invention placed individually and mutually at the distal ends and the proximal ends.

FIG. 17 is the previously described bipolar pacemaker system of FIG. 2 now showing various locations for the closed loop attenuator 205 of the present invention. As can be seen, the closed loop attenuator can be disposed anywhere along the lead systems or even around groupedtogether lead systems.

There is a down side to the closed loop current attenuator 205 of the present invention in that, all of this greatly increased current flow in the closed loop, does create heat. Referring back to FIG. 15, one can see that when the current ($i_{coupled}$) through coil 200 gets very large, that the current not only flows through capacitor 208 but also flows through the resistance 1.35 ohms of the coil itself. This creates an $I^2R$ loss, which is the formula for power. This power is converted from watts into heat energy, which is undesirable. Referring back to FIG. 17, it is desirable to have this benefit when the closed loop attenuator 205 is disposed near the distal electrodes so as to take away maximal induced RF energy away from them. As can be seen in FIG. 17, a desirable location for the closed loop attenuator would be along the length of the lead, in the blood stream of say, the right ventricle 110 or the right atrium 108. These are highly perfused areas, meaning that there is a lot of blood flow that would carry a lot of heat away from the closed loop attenuator of the present invention. Another acceptable location for the closed loop attenuator would be near the AIMD itself, which is generally placed in a pocket either under the skin or underneath the pectoral muscle. Having the closed loop attenuator placed away or distant from sensitive tissue, such as myocardial tissues or nerve tissues and instead in muscle or fat, makes heating in that location far less dangerous. Maximizing heat transfer out of the closed loop attenuator of the present invention will be described in a subsequent drawing.

Figure 18:
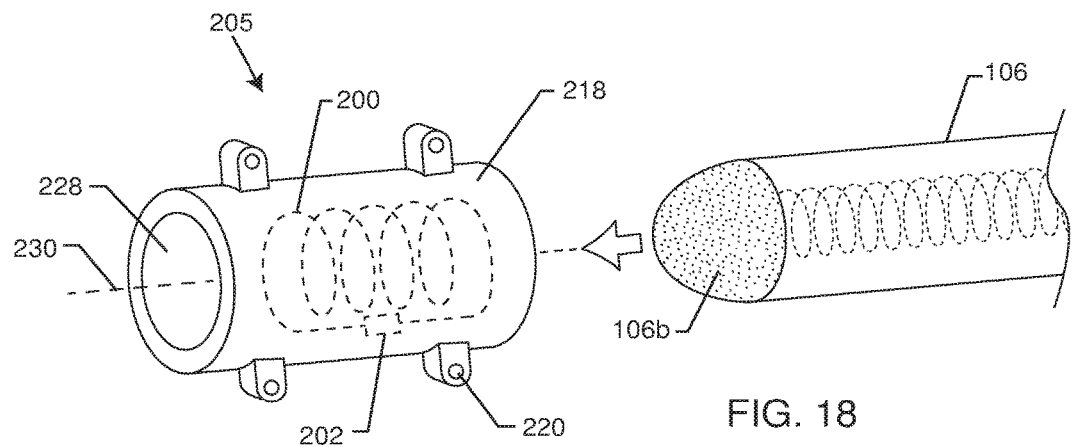
FIG. 18 is a perspective view of an exemplary embodiment of the present invention which can be placed over a separate implantable lead.

FIG. 18 of the present invention illustrates the closed loop attenuator 205 may be embedded in its own separate housing 218 that can be slipped on to a pre-existing lead body shown as 106 (in this case, having unipolar electrode 106b). Referring back to the closed loop attenuator 205 and its housing 218, one will see that one or more suture tabs 220 are included. The suture tabs 220 allow the surgeon to place stitches/sutures to thereby anchor the RF current attenuator assembly 205 in place. These sutures/stitches can be placed around the lead body 106 or through body tissues or both. As can be seen, an aperture 228 is formed by the housing 218 such that the aperture 228 is disposed through a center of the coiled conductor along a longitudinal axis 230.

Figure 19:
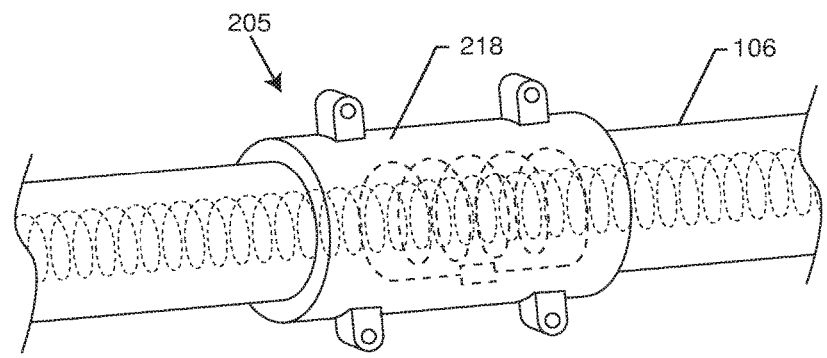
FIG. 19 is a perspective view of the structure of FIG. 18 now showing the separate implantable lead passing through the present invention.

FIG. 19 illustrates the closed loop attenuator assembly 205 as previously shown in FIG. 18 now slipped over the lead body 106. In other words, FIG. 19 shows the mating of the closed loop attenuator assembly 205 of the present invention placed onto the lead body 106.

Figure 20:
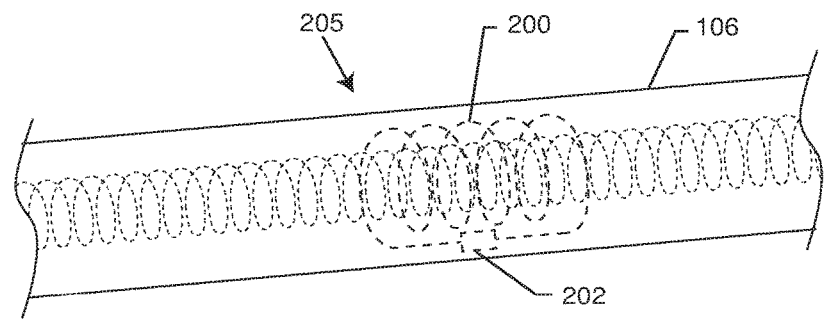
FIG. 20 is a perspective view of an embodiment of the present invention where the present invention is integrated into the structure of the implantable lead.

FIG. 20 illustrates that the closed loop attenuator 205 of the present invention can be designed into the lead body 106 thereby eliminating the need for a separate structure 218.

Referring back to FIG. 20, it is an essential property of the present invention that the conductor that forms the coil 200, of the current attenuator, be insulated. This is very important so that the individual turns of the coil do not short to each other (called a turn-to-turn short) or form electrical connection to any other surrounding materials, such as lead conductors, body tissues or the like.

Figure 21:
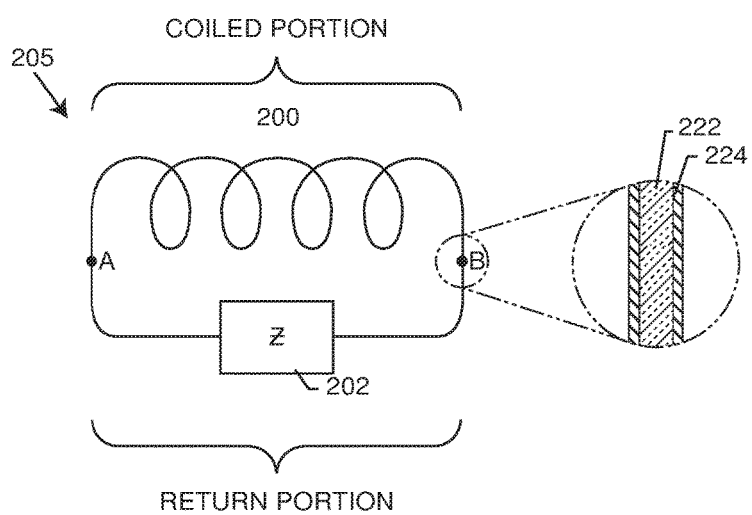
FIG. 21 is a simplified electrical schematic of the present invention now showing an internal conductive wire with an insulative outer coating.

FIG. 21 includes a blown-up section showing that the lead that forms the coil 200 includes a conductor 222, which is surrounded by an insulator 224, which can also be thought of as a dielectric. Furthermore, an embodiment of the present invention is when the impedance Z 202 is a capacitor and that the closed loop attenuator 205 be resonant at the MRI RF-pulsed frequency. Part of creating this resonance is to control the parasitic capacitance of the coil 200. One does this by controlling the type of insulation 224 and the thickness of the insulation 224. By controlling the type of insulation, one can control its dielectric constant and therefore, the amount of parasitic capacitance that develops. Of course, the balance of the capacitor is provided by circuit element 202, which in the preferred embodiment is a discrete capacitor.

Figure 22:
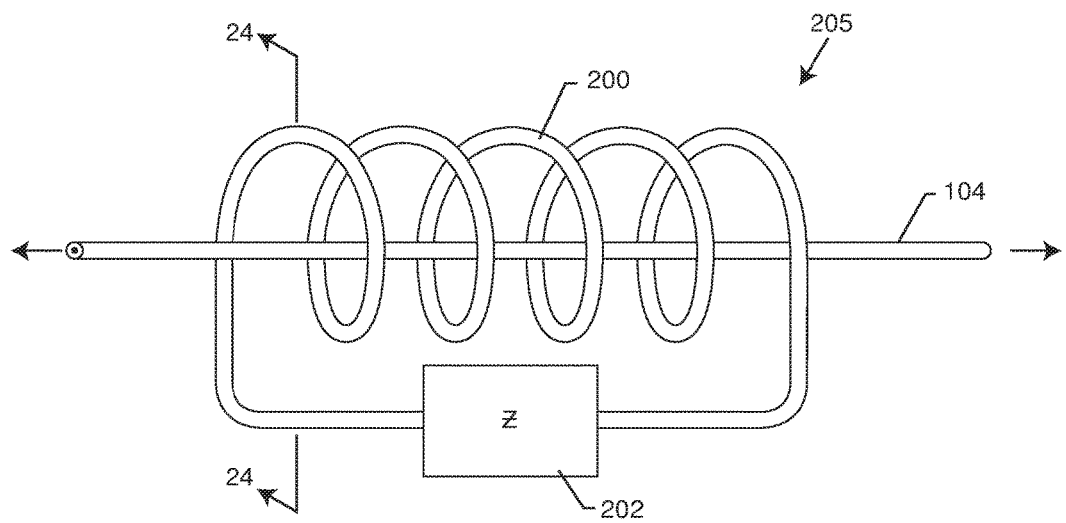
FIG. 22 is a simplified three-dimensional view of the present invention clarifying how the coil 200 is wound about the internal lead conductor.

FIG. 22 illustrates the three-dimensional shape of the closed loop attenuator 205, including its coil 200 and its impedance element 202.

Figure 23:
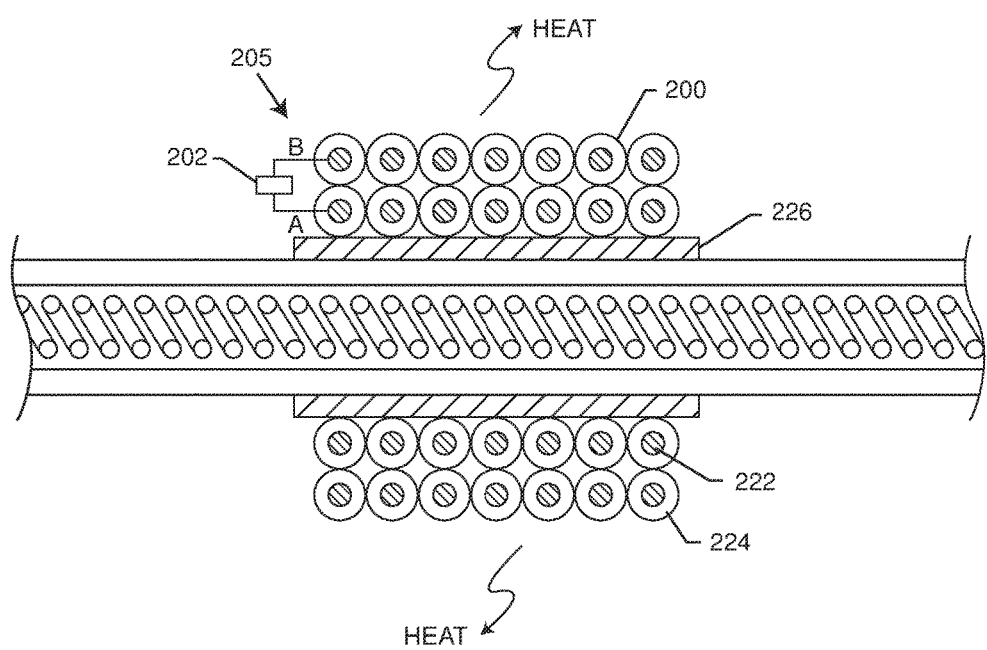
FIG. 23 is a sectional view of the present invention showing a more densely wound coil of the present invention and how heat can be dissipated outwardly into body tissue and/or fluids.

All of the preceding drawings to FIG. 23 are actually inaccurate in that, for ease of illustration, the coils have been shown loosely wound. FIG. 23 illustrates that the actual coils that form inductor 200 would be very tightly packed. FIG. 23 illustrates one embodiment wherein, the coils were first wound in one direction, very tightly and then wound back on themselves very tightly, such that the impedance element 202 can be used to connect their two open ends (A and B). As described, element 202 can be a short or in a preferred embodiment, a small chip capacitor. Element 202 can be any of the previously described impedance elements as shown in FIGS. 6 through 10A. As can be understood by those skilled in the art, the ends A and B can be adjacent to one another as shown here or reside on opposite ends of the coil 200, as it is dependent upon the winding used to create the closed loop attenuator 205.

Starting at a first coil end A, the innermost coil can proceed to be wound to the right and then the coil 200 is wound upon itself back to the left so it stops at second coil end B. The outermost portion of the wound coil 200 is a return coiled conductor portion that then allows ends A and B to be adjacent to one another. As is understood by those skilled in the art this embodiment has two windings, but three, four, five, six or any number of windings are possible.

The electrical insulation that surrounds conductor 222 may be electrically insulative but highly thermally conductive. This allows the heat generated within the closed loop attenuator 205 to be readily transferred into surrounding body tissues and fluids, such that not too much temperature rise occurs. Body fluids, such as moving blood, can absorb a substantial amount of heat energy without subsequent temperature rise. However, when placed in a poorly perfused location, such as in the spinal nerve root, even a small amount of heat can result in a significant temperature rise in that poorly perfused area. In other words, location is important.

Referring once again to FIG. 23, the closely wound coils of inductor 200 can be wound on a mandrel 226. Commonly available coil winders and materials now allow one to wind the coils on the mandrel 226 and then heat up the structure, such that the surrounding turns stick to each other. This allows the mandrel 226 to be removed leaving the coil structure 220 free-standing.

The closed loop attenuator 205 of the present invention is particularly effective when it is disposed over an implantable lead wire that embodies helically or spirally wound coils. The use of helix or multiple spirals are very common in cardiac applications where the lead has to be highly flexible and be able to withstand.

Although several embodiments have been described in detail for purposes of illustration, various modifications may be made to each without departing from the scope and spirit of the invention. Accordingly, the invention is not to be limited, except as by the appended claims.

What is claimed is:
1. An implantable medical lead, comprising:
 a) at least one lead conductor extending from a lead conductor proximal end to a lead conductor distal end, wherein the lead conductor proximal end is electrically connectable to electronic circuits of an active implantable medical device;

b) an electrode that is conductively connected to the lead conductor distal end, wherein the electrode is contactable with biological cells; and c) at least one closed loop attenuator comprising at least one insulated coiled conductor extending in a coiled shape around at least a portion of the at least one lead conductor, the coiled conductor extending from a coiled conductor first end to a coiled conductor second end, wherein the coiled conductor first end is electrically connected to the coiled conductor second end by a return path.

2. The lead of claim 1, wherein the return path comprises a return conductor electrically connecting the coiled conductor first end to the coiled conductor second end, and wherein the return conductor is either a short, or at least one of a capacitor, a resistor, and a resistor in series with a capacitor is in series along the return conductor.

3. The lead of claim 1, wherein the at least one closed loop attenuator comprising the at least one insulated coiled conductor extending in the coiled shape around at least a portion of the at least one lead conductor comprises part of a catheter.

4. The lead of claim 1, wherein the at least one closed loop attenuator comprises a plurality of coiled conductors that are electrically connected in series.

5. The lead of claim 1, wherein the at least one closed loop attenuator comprising the at least one insulated coiled conductor and the return path is not electrically connected to the at least one lead conductor.

6. The lead of claim 1, wherein the at least one insulated coiled conductor of the closed loop attenuator is insulated from the at least one lead conductor by an insulator that is electrically insulative and thermally conductive.

7. An implantable medical lead, comprising:

a) at least one lead conductor extending from a lead conductor proximal end to a lead conductor distal end, wherein the lead conductor proximal end is electrically connectable to electronic circuits of an active implantable medical device;

b) an electrode that is conductively connected to the lead conductor distal end, wherein the electrode is contactable with biological cells; and c) at least one closed loop attenuator comprising at least one insulated coiled conductor extending in a coiled shape around at least a portion of the at least one lead conductor, the coiled conductor extending from a coiled conductor first end to a coiled conductor second end, d) wherein the coiled conductor first end is electrically connected to the coiled conductor second end by a return path comprising an impedance element.

8. The lead of claim 7, wherein the impedance element comprising the return path comprises at least one of a short, a capacitor, a resistor, and a resistor in series with a capacitor.

9. The lead of claim 7, wherein the at least one closed loop attenuator comprising the at least one insulated coiled conductor extending in the coiled shape around at least a portion of the at least one lead conductor comprises part of a catheter.

10. The lead of claim 7, wherein the at least one closed loop attenuator comprises a plurality of coiled conductors that are electrically connected in series.

11. The lead of claim 7, wherein the at least one closed loop attenuator comprising the at least one insulated coiled conductor and the return path is not electrically connected to the at least one lead conductor.

12. The lead of claim 7, wherein the at least one insulated coiled conductor of the closed loop attenuator is insulated from the at least one lead conductor by an insulator that is electrically insulative and thermally conductive.

* * * * *